United States Patent
Craig et al.

(10) Patent No.: US 12,102,288 B2
(45) Date of Patent: *Oct. 1, 2024

(54) MULTI-USE ENDOSCOPES AND ASSOCIATED SYSTEMS AND METHODS

(71) Applicant: ELEMENTS ENDOSCOPY, INC., Minneapolis, MN (US)

(72) Inventors: Brian H. Craig, Minnepolis, MN (US); Dwight Meglan, Westwood, MA (US)

(73) Assignee: ELEMENTS ENDOSCOPY, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/490,237

(22) Filed: Oct. 19, 2023

(65) Prior Publication Data

US 2024/0041302 A1 Feb. 8, 2024

Related U.S. Application Data

(63) Continuation of application No. 16/769,813, filed as application No. PCT/US2018/064984 on Dec. 11, 2018, now Pat. No. 11,826,023.

(Continued)

(51) Int. Cl.
*A61B 1/00* (2006.01)
*A61B 1/018* (2006.01)
(Continued)

(52) U.S. Cl.
CPC ........ *A61B 1/00142* (2013.01); *A61B 1/0002* (2013.01); *A61B 1/00057* (2013.01);
(Continued)

(58) Field of Classification Search
CPC ... A61B 1/00105; A61B 90/98; A61B 1/0002; A61B 1/00057; A61B 1/00066;
(Continued)

(56) References Cited

U.S. PATENT DOCUMENTS 3,858,577 A    1/1975  Bass et al.
5,711,756 A *  1/1998  Chikama ............. A61B 1/0607
                                              600/172
(Continued)

FOREIGN PATENT DOCUMENTS

DE   10 2009 038979 A1   3/2011
JP       2009273571 A   11/2009
WO         9315648 A1    8/1993

OTHER PUBLICATIONS

The International Search Report and The Written Opinion of the International Searching Authority issue date Jul. 9, 2019 in international application No. PCT/US2018/064984.

*Primary Examiner* — Michael J Carey
*Assistant Examiner* — Stephen Floyd London
(74) *Attorney, Agent, or Firm* — MEDLER FERRO WOODHOIUSE & MILLS PLLC

(57) ABSTRACT

An endoscope having an outer sheath, a handle, an optical window and an optical module. The outer sheath includes a lumen extending between a proximal end and a distal end thereof. The handle is mounted at the proximal end of the outer sheath and includes an external data connector. The optical window is removably and sealingly mounted at the distal end of the outer sheath. The optical module is removably disposed within the distal end of the outer sheath and includes an integrated image sensor, an optical lens, and an optical module connector. The optical module connector is configured for selective disconnection from and reconnection to a mating line connector in electrical communication with the external data connector of the handle. The optical module and the outer sheath further include one or more alignment features configured to ensure correct radial and axial positioning.

20 Claims, 7 Drawing Sheets

Related U.S. Application Data

(60) Provisional application No. 62/597,865, filed on Dec. 12, 2017.

(51) Int. Cl.
*A61B 1/05* (2006.01)
*A61B 1/06* (2006.01)
*A61B 90/98* (2016.01)

(52) U.S. Cl.
CPC ...... *A61B 1/00066* (2013.01); *A61B 1/00096* (2013.01); *A61B 1/00105* (2013.01); *A61B 1/00124* (2013.01); *A61B 1/00128* (2013.01); *A61B 1/00135* (2013.01); *A61B 1/018* (2013.01); *A61B 1/05* (2013.01); *A61B 1/06* (2013.01); *A61B 90/98* (2016.02)

(58) Field of Classification Search
CPC ............ A61B 1/00096; A61B 1/00124; A61B 1/00128; A61B 1/00135; A61B 1/018; A61B 1/05; A61B 1/06; A61B 1/00142; A61B 1/053; A61B 1/00018; A61B 1/00062; A61B 1/00101; A61B 1/00114; A61B 1/00137; A61B 1/00144; A61B 1/055; A61B 1/121; A61B 1/122; A61B 1/123; A61B 1/125; A61B 1/00103; F21L 4/06; H04N 23/57
USPC ........................................................ 600/104
See application file for complete search history.

(56) References Cited

U.S. PATENT DOCUMENTS

| | | |
|---|---|---|
| 6,019,719 A | 2/2000 | Schulz et al. |
| 2003/0205029 A1 | 11/2003 | Chapolini et al. |
| 2004/0143162 A1* | 7/2004 | Krattiger ............ A61B 1/00101 600/129 |
| 2005/0182299 A1* | 8/2005 | D'Amelio .......... G02B 23/2423 600/172 |
| 2005/0277808 A1* | 12/2005 | Sonnenschein ........ A61B 1/053 600/153 |
| 2006/0217594 A1* | 9/2006 | Ferguson ............. A61B 1/0676 600/179 |
| 2007/0049794 A1* | 3/2007 | Glassenberg .......... A61B 1/042 600/179 |
| 2007/0106119 A1* | 5/2007 | Hirata ................ G02B 23/2423 600/179 |
| 2007/0142711 A1* | 6/2007 | Bayer ................ A61B 1/00101 600/172 |
| 2007/0162095 A1* | 7/2007 | Kimmel ................. A61B 1/042 600/172 |
| 2007/0167681 A1 | 7/2007 | Gill et al. |
| 2010/0204546 A1 | 8/2010 | Hassidov et al. |
| 2010/0298640 A1 | 11/2010 | Oneda et al. |
| 2011/0028790 A1* | 2/2011 | Farr ..................... A61B 1/0676 600/187 |
| 2012/0040305 A1* | 2/2012 | Karazivan .......... A61B 1/00087 433/29 |
| 2012/0100729 A1 | 4/2012 | Edidin et al. |
| 2012/0329312 A1* | 12/2012 | Oue ....................... G02B 23/26 439/452 |
| 2014/0142383 A1* | 5/2014 | Blumenzweig .... A61B 1/00057 600/110 |
| 2014/0204188 A1 | 7/2014 | Ariyoshi et al. |
| 2015/0112132 A1 | 4/2015 | Neiman et al. |
| 2016/0296104 A1 | 10/2016 | Smith |
| 2017/0035277 A1 | 2/2017 | Kucharski et al. |
| 2018/0028250 A1 | 2/2018 | O'Connor |
| 2018/0084162 A1 | 3/2018 | Stephenson |
| 2018/0132703 A1 | 5/2018 | Reever et al. |
| 2021/0186316 A1* | 6/2021 | Thommen ................ A61B 1/07 |

\* cited by examiner

MULTI-USE ENDOSCOPES AND ASSOCIATED SYSTEMS AND METHODS

CROSS-REFERENCE TO RELATED APPLICATIONS

This application is a continuation of U.S. application Ser. No. 16/769,813, filed Jun. 4, 2020, now allowed, which is a national stage application of PCT/US2018/064984, filed Dec. 11, 2018, which claims priority to U.S. Appl. No. 62/597,865, filed Dec. 12, 2017, each of which is incorporated by reference herein in its entirety.

TECHNICAL FIELD

The present disclosure relates generally to multi-use endoscopes and associated systems and methods.

BACKGROUND

An endoscope is an illuminated optical, typically slender and tubular instrument used to look deep into the body. It is used in procedures called endoscopy. The endoscope may have a rigid or flexible casing. Additionally, the endoscope may be used for diagnostic or therapeutic procedures.

Nearly all endoscopes are designed as multi-use devices, or devices that are used over multiple procedures and multiple patients. They are sold as capital to a user, meaning they are sold once and used multiple times over an extended period. Since multi-use endoscopes are used inside patients' bodies they must be cleaned or decontaminated between procedures to not transmit infectious diseases among patients contacted by the same endoscope. Today this cleaning is done at the clinical site of care, e.g., the hospital or clinic. Manufacturers who sell multi-use endoscopes are not involved in reprocessing of the devices and as a result assume no responsibility in ensuring endoscope fitness-for-use beyond validating the cleaning protocols that should be used at the clinical site of care.

When cleaning protocols are strictly followed they have been proven to sufficiently sterilize the endoscopes. However, cleaning steps are largely manual and may be intentionally or unintentionally skipped or not sufficiently completed, which may result in dirty endoscopes that can transmit infectious diseases among patients.

An emerging solution to address dirty endoscopes is a disposable, single-use endoscope where the device is provided to the customer in a sterile, ready-for-use condition. When the procedure is completed, these endoscopes are discarded and not meant to be used in another patient. These disposable endoscopes at least reduce the risk of cross-contamination between patients, but they typically cost more per procedure than multi-use endoscopes and may offer lower performance. The single-use endoscope business model is similar to the current multi-use endoscope model to the extent that the endoscope is sold only once to the end user. There is not a selling model today where the same endoscope can be used multiple times and is sold to a user in a ready-for-use condition before or after every use or on a per use basis. Additionally, there is currently no endoscope designed to specifically facilitate this selling model.

Since multi-use endoscopes are used over many procedures it is expected that the endoscope performance will degrade unlike single-use endoscopes. This performance degradation can occur rapidly, such as when an endoscope is dropped and the internal components are damaged or it can occur progressively over time through repeated clinical use and cleaning. It can be difficult to know the endoscope's performance capability relative to its original specifications because the endoscopes are not performance-tested rigorously between cases. As a result, a clinician may not be using optimally-performing endoscopes in critical clinical procedures.

Should sufficient endoscope performance degradation be noticed by the clinical user, it is possible to send the endoscope to the original manufacturer or a third party for repair/refurbishment or exchange for a previously repaired device. This is usually done via a standing service contract with the original manufacturer structured at time of sale or contracted as needed. It is important to note that any party (original endoscope manufacturer or third party) repairing or refurbishing a multi-use endoscope under a service contract is losing profit with every endoscope serviced. As a result, the repair entity under a service contact is not incentivized to perform service at all and would prefer to extend time to or between servicing as long as possible.

The original manufacturer or third party will attempt to repair or service the device back to its original performance specifications and obtain more usable life for the device, if possible. Repair or refurbishment is not done after every clinical case, but is done only when performance of the device has been noticeably compromised, either after extended use over multiple procedures or suddenly, e.g., accidental damage.

The other challenge with a multi-use endoscope in a capital-based business model is that the multi-use feature is exploited to spread the acquisition cost over many uses and longer time. This means that a purchase decision by an end user forces the same technology to be used in every case for an extended period of time, typically years. The technology advancements in endoscopy can be rapid which means that after only a short portion of the usable life of the endoscope, it may already be antiquated. This means that the end user is forced by a financial incentive to use inferior technology, which could affect clinical outcomes. The only alternative is for the user to upgrade to a new capital asset at an incremental expense, perhaps resulting in larger than anticipated expense for the end user. Additionally, since re-using a device means that the same level of technology is used in multiple cases, it may mean inefficient spending by the clinical end user by either (a) under-spending in some cases and not utilizing the available preferred or optimal endoscope technology and thereby potentially effecting clinical outcomes or (b) over-spending in some cases by utilizing advanced technology that is not clinically necessary for a particular patient.

Today, the business transaction between the original endoscope manufacturer and the customer ends after the first sale, thus leaving the cleaning/sterility and assessing device performance obligations to the end user in a feature-constrained and cost-inefficient manner. This disclosure proposes endoscope design elements and business models that address the issues of dirty endoscopes, uncertain device performance following previous uses, endoscope affordability, and optimal per-procedure device selection.

DETAILED DESCRIPTION

The present disclosure relates generally to multi-use endoscopes and associated systems and methods. Specific details of several embodiments of the present technology are described herein with reference to FIGS. 1-7. Although many of the embodiments are described with respect to multi-use endoscope devices, systems, and methods, other embodiments in addition to those described herein are within the scope of the present technology. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of an endoscope). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

Figure 1:
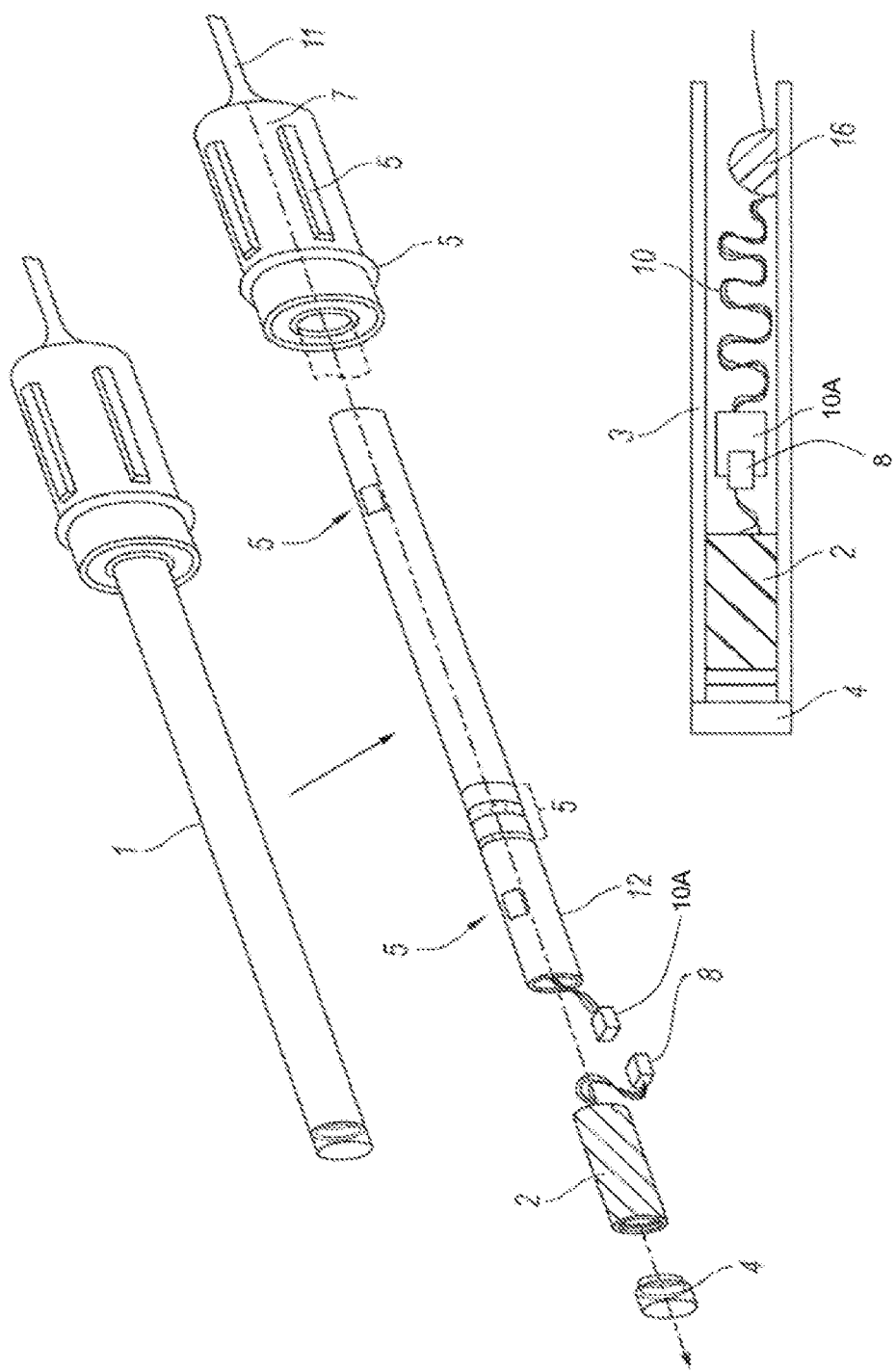
FIG. 1 shows isometric and cross-sectional views of an endoscope system configured in accordance with embodiments of the present technology.

FIG. 1. System Overview

The reprocessable Endoscope (1) is limited to a specific number of uses and includes a re-usable Optical Module (2) and single-use or limited re-use Outer sheath (12) and single-use or limited re-use Optical Window (4). The outer body (3) includes externally exposed elements including the Outer sheath (12) mounted thereabout and Optical Window (4) and Handle (7). Outer body (3) further includes one or more inner lumens extending therethrough. In some embodiments, the Endoscope (1) may have only a single-layer tube. Therefore, the terms Outer body (3) and Outer sheath (12) may be used interchangeably throughout the description. For example, the Optical Module (2) may be removably mounted in a lumen of Outer body (3) or Outer sheath (12).

The Optical Module (2) is a high value, high cost assembly and it can be easily removed and transplanted into a new low value, low cost Outer sheath (12) when the previous Outer Body (3) deteriorates or is selectively replaced.

The Endoscope (1) can be cleaned a number of times (machine cleaning) before the external Optical Window (4) mounted on the distal end of Outer Sheath (12) deteriorates. Alternatively, this Optical Window (4) can be replaced after every cleaning cycle.

It is possible to remove the Optical Module (2) from the Outer Sheath (12) without the need to initially clean the Outer Body (3) and without contaminating the Optical Module (2) during this process.

The reprocessable Endoscope (1) has a modular design, comprising the re-usable Optical Module (2) which is sealed within the limited re-use Outer Sheath (12) and the Optical Window (4). The Outer Body (3) includes the Handle (7) with an external data connection (11) extending therefrom.

The Optical Module (2) can be accessed proximally by removing the Handle (7) or distally by removing the Optical Window (4) which are sealed to prevent fluid ingress and human tissue contamination.

The Optical Module (2) is easily removed from the Outer Sheath (12) without contaminating the surface of the Optical Module (2) such that the module may not require cleaning before re-use.

The Optical Window (4) of the Outer Body (3) may be easily removed and replaced after every cleaning cycle or after several cleaning cycles.

Alternatively, the Optical Window (4) may be permanently connected to the outer sheath (12) requiring replacement between uses should it be damaged.

The Handle (7) contains mechanical and visible alignment and holding features (5) which will enable an effective mechanical interface for automated machine cleaning of the Endoscope (1).

Figure 2:
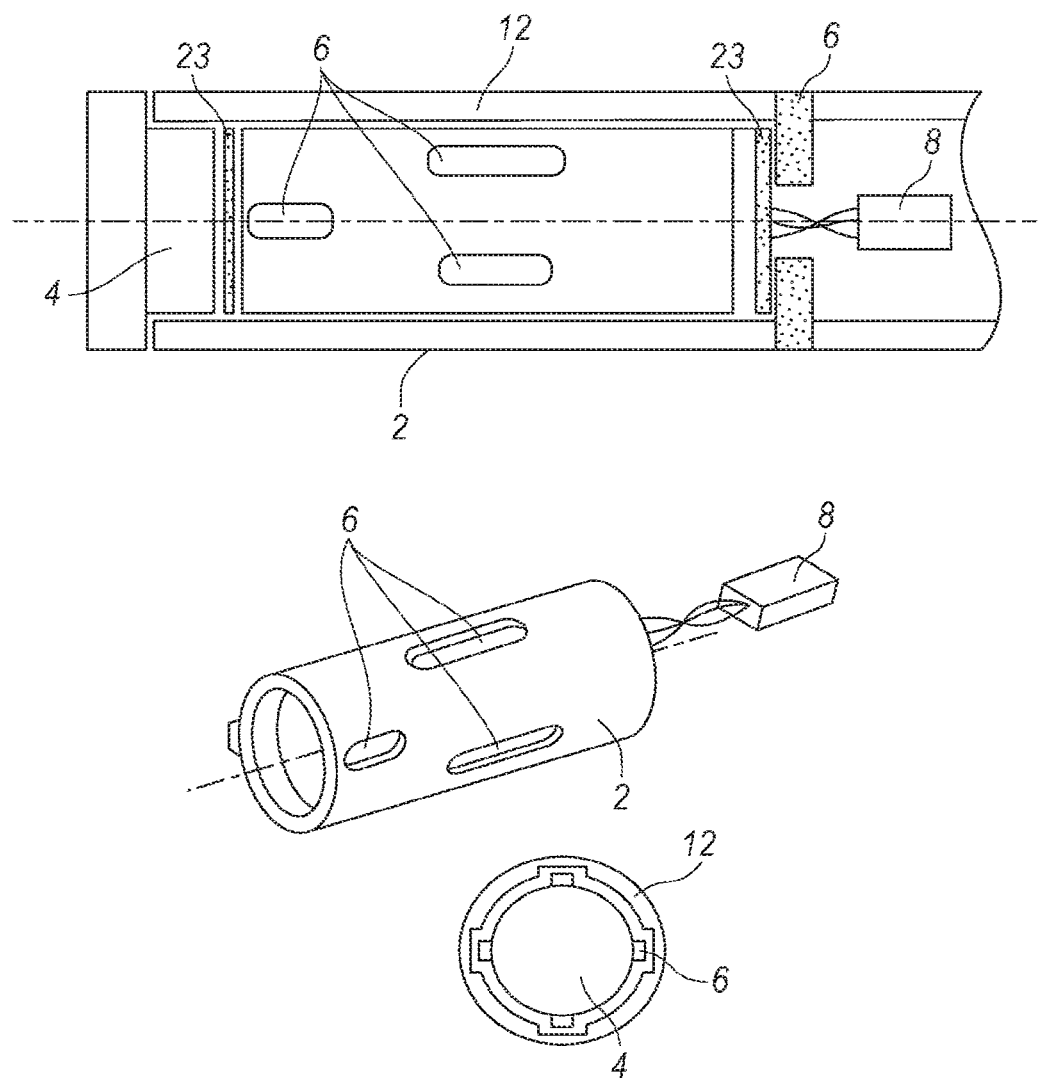
FIG. 2 shows isometric, cross-sectional, and front views of an optical module configured in accordance with embodiments of the present technology.

FIG. 2. Optical Module Outer Design

The Optical Module (2) and Outer Sheath (12) both contain alignment features (6) to ensure the correct radial and axial positioning of the Optical Module (2) relative to the Handle (7) and Optical Window (4).

The Optical Module (2) may contain features to enable the external adjustment of the position and alignment of internal optical components prior to being permanently fixed.

A sealing ring (23) may be disposed between the Optical Module (2) and optical window (4) to create a seal with the Outer Sheath (12) to prevent fluid or tissue ingress.

A sealing ring (23) may be used between optical module (2) and optical window (4) and outer body (3) to assist with fit and avoid rattling/motion while in use.

Figure 3A:
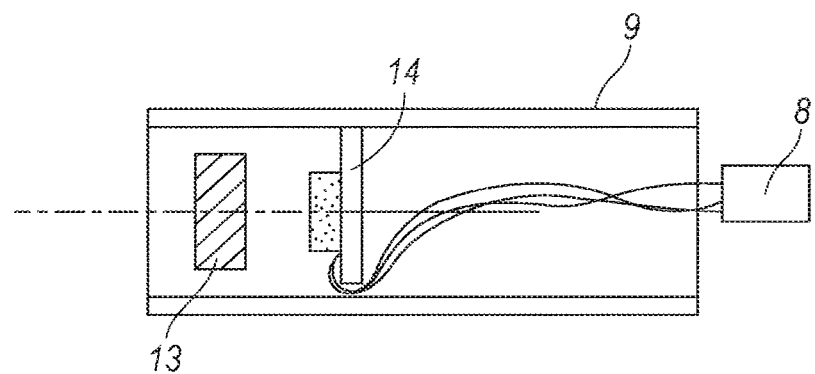
FIGS. 3A and 3B are cross-sectional views of optical modules configured in accordance with embodiments of the present technology.
Figure 3B:
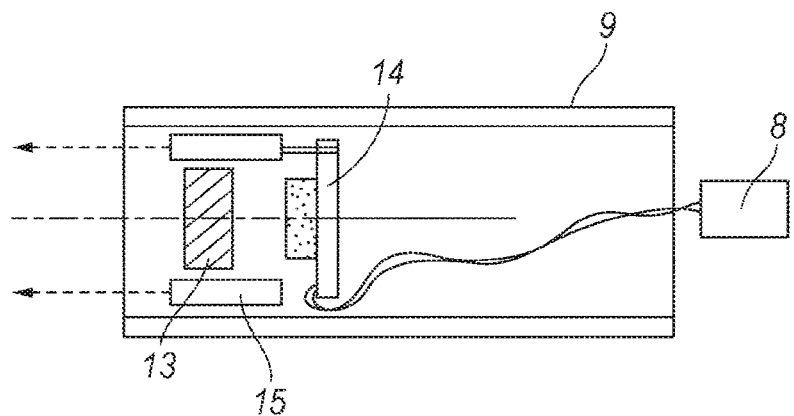

FIGS. 3A and 3B. Optical Module Internal Design

The Outer Body (3) contains electrical connections (11) extending proximally from the Handle (7) to enable connection to an external system. This connection (11) may be via a USB-type cable, e.g., a cable having any of various USB-type connectors including but not limited to A, B, and C types and "micro" and "mini" versions. These connections may be waterproof or water resistant. The connection (11) may have a reversible locking mechanism to avoid inadvertent disconnection during use, transport, or processing.

The Optical Module (2) connects electrically to an internal electrical connector (10A) within the Outer Sheath (12), possibly via a USB connector (8). If the Optical Window (4) is removed from the distal end of the Outer Sheath (12) then there should be sufficient slack length of a Mating Line or Cable (10) to ensure that the electrical connector (10A) can be accessed outside of the Outer Sheath (12), as shown in FIG. 1. Stated another way, the Optical Module (2) includes an Optical Module Connector (8) that is configured to mate with a Mating Line Connector (10A) of the Line (10), as shown in FIG. 1.

The method of electrical connection between the Optical Module (2) and the Outer Sheath (12) is robust to prevent accidental dis-connection during use. This may be achieved by providing one or more mechanical anchoring points (16) on the inner wall defining the lumen of the Outer Sheath (12).

The Optical Module (2) may require a tool to remove it from the Outer Sheath (12)—either from the distal or proximal ends of the Endoscope (1). The Optical Module may contain features to help lock it to the tool.

The Optical Module (2) can be in two different configurations. In a first configuration (FIG. 3A) Optical Module (2) comprises an outer casing (9), a lens or lens assembly (13), a PCB (printed circuit board) containing a camera chip (14) and a connector (8) that may be directly mounted on the PCB (not shown) or attached to the PCB via a flexible electrical cable. In this configuration, an illumination source is separate from the optical module and must be integrated elsewhere into the endoscope body. In a second configuration (FIG. 3B), Optical Module (2) comprises an outer casing (9), a lens or lens assembly (13), an LED lighting system (15), a PCB containing a camera chip (14) and a connector (8) that may be directly mounted on the PCB (not shown) or attached to the PCB via a flexible electrical cable.

FIGS. 4A-4D. Optical Window Fixation Options

The Optical Window (4) may be attached to the Outer Sheath (12) via a screw thread (17). One or more Flats (29) on the Optical Window (4) may be used to enable easy removal of the Optical Window (4), e.g. using a tool. See FIG. 4A.

In an alternative configuration, the Optical Window (4) and the Optical Module (2) may contain Interlocking Features (18) to control the rotational orientation of the Optical Module during and after assembly. The Optical Module (2) may be pressed lightly against the Optical Window (4) with a Proximal Spring Feature (19), e.g., a coil spring to control the axial position of the Optical Module (4). See FIG. 4B.

In another configuration, to control the axial position of the Optical Module (2) relative to the Outer Sheath (12), the Optical Module (2) may have a Distal Spring Feature (20), e.g., leaf springs to react against the Optical Window (4) and thereby restrain the proximal end of Optical Module (2) against a Step Feature (21), e.g., shoulder or pocket formed on the inner surface of the Outer Sheath (12). There may be additional corresponding tab and notch features (22) in the Optical Module (2) and the Outer Sheath (12) to control the relative rotational/radial position of the Optical Module (2) to the Outer Sheath (12). See FIG. 4C.

In another configuration, the Optical Module (2) may be press-fit into a Receptacle (24) within the Optical Window (4) which is then welded or bonded to a distal Neck (25) on the Outer Sheath (12). Removal of the Optical Window (4) would also result in removal of the outer sheath (12). The optical module (2) can be extracted via the proximal or handle end of the outer sheath (12). The Handle (7) may contain a feature such as a plug or removable wall which would enable extraction of the Optical Module (2) through the proximal end of the Outer Body (3). This method of extracting the Optical Module (2) may be required if the Optical Window (4) is integrated into the Outer Sheath (12) and cannot be easily removed. See FIG. 4D.

In accordance with the above alternative embodiments, the Optical Window (4) may be designed either for rapid exchange, e.g., simple, non-destructive detachment from and reattachment to the Outer Sheath (12) or for permanent or semi-permanent assembly so that removal would prevent re-attachment and re-use.

Figure 5A:
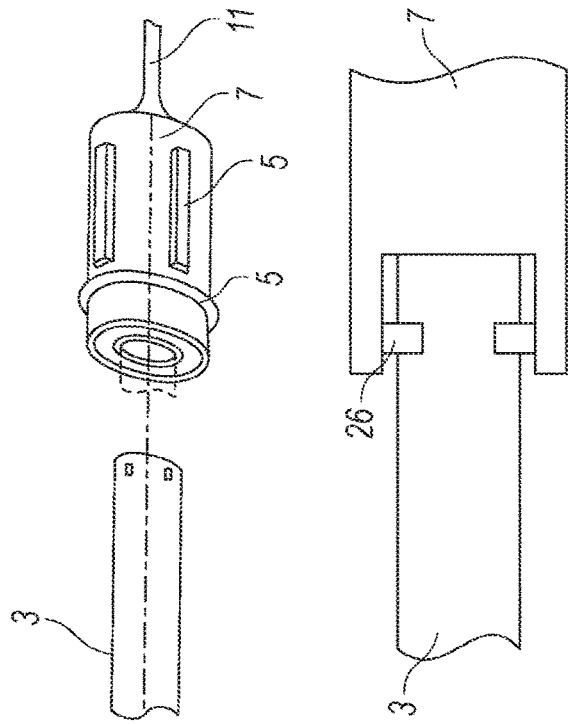
FIGS. 5A-5C are isometric and cross-sectional views of handle connections configured in accordance with embodiments of the present technology.
Figure 5B:
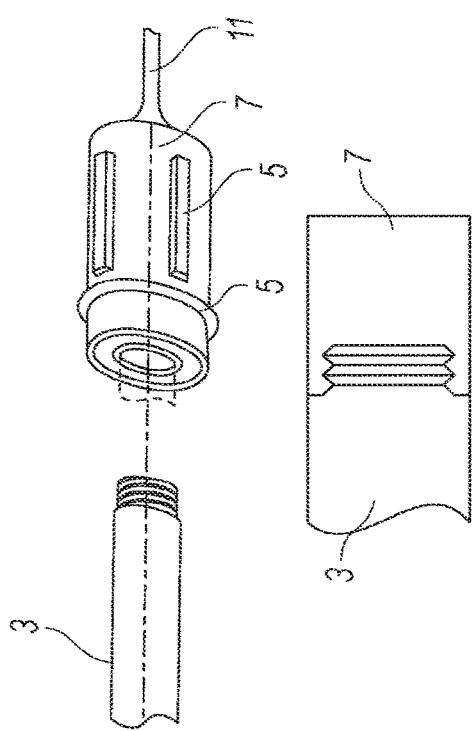
Figure 5C:
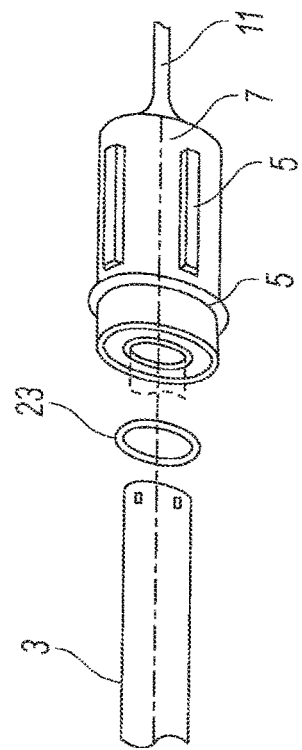

FIGS. 5A-5C. Handle Connection

Figure 4A:
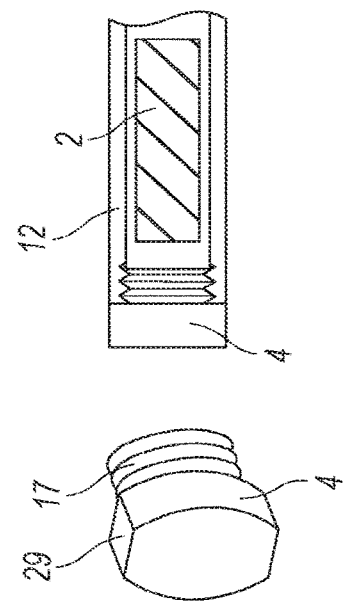
FIGS. 4A-4D are isometric and cross-sectional views of optical windows and optical modules configured in accordance with embodiments of the present technology.
Figure 4B:
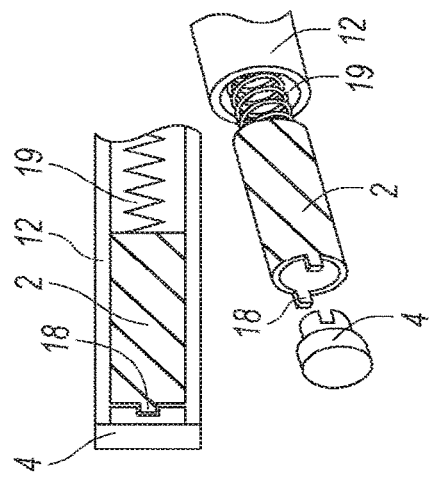
Figure 4C:
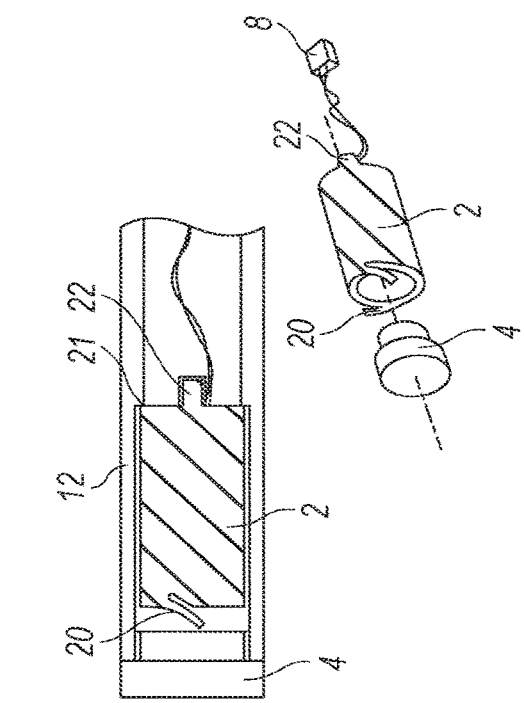
Figure 4D:
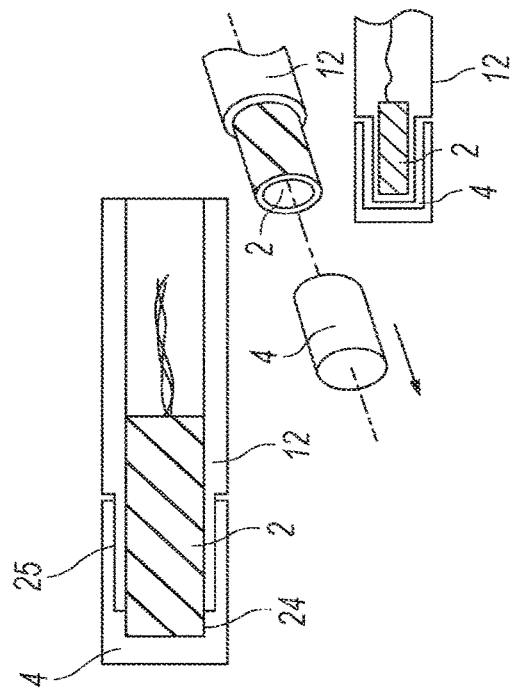

The Handle (7) may be attached to the Outer Sheath (12) via a screw thread (17) similar to those shown in FIG. 4A regarding attachment of Optical Window (4). Holding features on the handle (7) may be used to enable easy separation from Outer Sheath (12).

In an alternative configuration, the Handle (7) may have retractable/deployable Teeth (26) or detents that can lock into mating holes in the Outer Sheath (12) to lock the Handle (7) and Outer Sheath (12) together.

A Sealing Ring (23) may be used between the Handle (7) and the Outer Sheath (12) to create a seal to prevent fluid or tissue ingress.

Figure 6:
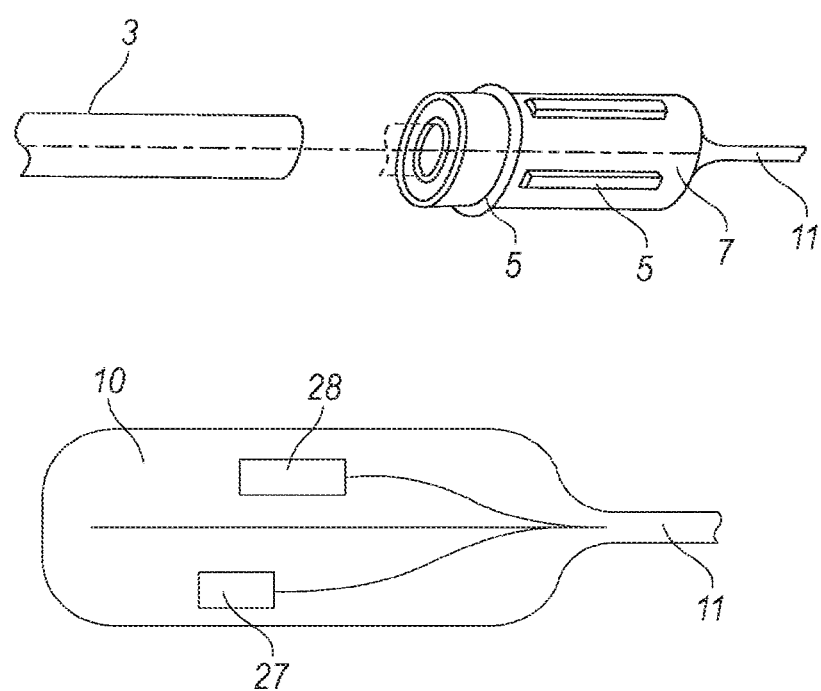
FIG. 6 shows isometric and cross-sectional views of handles configured in accordance with embodiments of the present technology.

FIG. 6. Handle Internal Components

The Handle (7) may contain a radio-frequency identification (RFID) chip (28) or other identification device(s) for quantifying the number of endoscopes in a container without requiring physical, manual counting, and potential contamination of the person doing the counting.

The Handle (7) may alternatively, or additionally contain an RFID chip (28) or other technology that prevents device from functioning after a single use, e.g. after connection to an external instrument during a clinical procedure. Such a re-use prevention component may prevent cross-contamination between patients, and can be replaced or re-set during reprocessing of the endoscope.

The Handle (7) may alternatively, or additionally, contain a Memory Module (27) to collect and record performance information from the device during clinical use. Such information may indicate the need for replacement of under-performing sub-components during reprocessing of the endoscope.

The Handle (7) may alternatively, or additionally, contain a Memory Module (27) to record unique identification of components used in device. Such information regarding installed components may inform replacement decisions based, for example on known reprocessing cycle life of a component or on a desire to upgrade the endoscope to a higher level of technology.

From the foregoing, it will be appreciated that specific embodiments of the technology have been described herein for purposes of illustration, but that various modifications may be made without deviating from the scope of the technology. Accordingly, the technology is not limited except as by the appended claims.

FIG. 7. Methods

Figure 7:
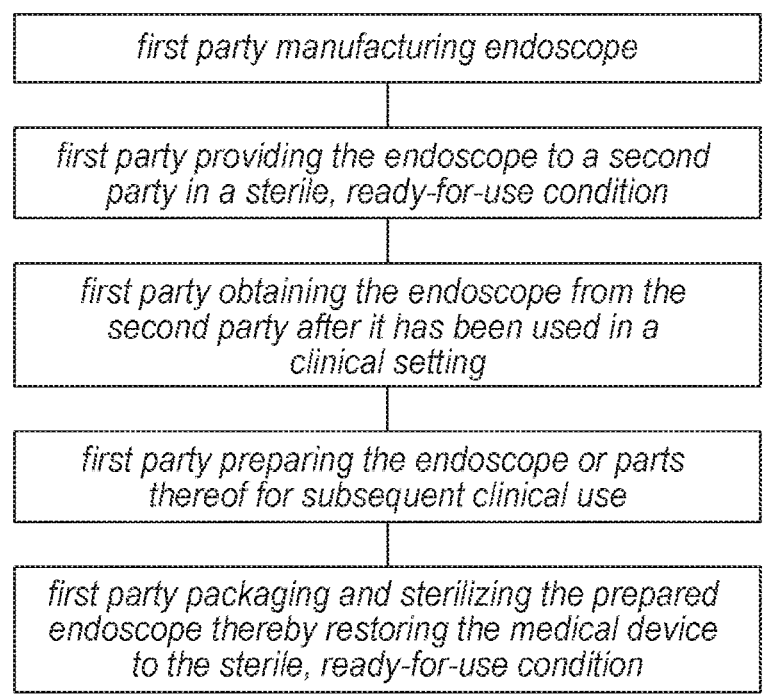
FIG. 7 is flow diagram of a method or process in accordance with embodiments of the present technology.

FIG. 7 is a flow diagram of a method or process for handling an endoscope in accordance with the present technology. As shown in FIG. 7, the method can include a first party manufacturing the endoscope. In some embodiments, the first party can manufacture the endoscope according to proprietary manufacturing specifications of the first party. The method can further include the first party providing the endoscope to a second party in a sterile, ready-for-use condition. In the illustrated embodiment, the method further includes the first party obtaining the endoscope from the second party after the endoscope has been used in a clinical setting, and the first party preparing the endoscope (or parts thereof) for subsequent clinical use. In some embodiments, the first party can prepare the endoscope (or parts thereof) for clinical use by: (i) cleaning and decontaminating the endoscope, (ii) testing system and component performance by connecting the endoscope to a proprietary and automated firmware and software testing protocol, (iii)

automated visual assessment of an outer body of the endoscope to assess for defects, markings, scratches or indentations from shipping or use that would visually deviate from original de novo parts, (iv) removing an optical window from an endoscope sheath distal end, (v) removing and electrically disconnecting an optical module from the endoscope, (vi) requalifying the optical window and the optical module against the proprietary manufacturing specifications of the first party, (vii) electrically connecting and assembling an optical module in the endoscope, and/or (viii) assembling an optical window on the endoscope sheath distal end. The method can further include the first party packaging and sterilizing the prepared endoscope to thereby restore the medical device (e.g., endoscope) to the sterile, ready-for-use condition. One or more of the above steps in preparing the endoscope (or parts thereof) for clinical use may be performed using processing equipment that can decontaminate, clean, disassemble, and reassemble the endoscope autonomously, semi-autonomously or under manual control. The endoscope may have external markings and/or physical features configured for tracking, aligning, and mating the device to manufacturing, processing and/or reprocessing equipment.

EXAMPLES

Several aspects of the present technology are set forth in the following examples.

1. An endoscope, comprising:
   an elongate outer sheath having a lumen extending between proximal and distal ends thereof, the sheath having external markings and/or physical features configured for tracking, aligning, and mating the sheath to manufacturing and reprocessing equipment;
   a handle removably and sealingly mounted at the sheath proximal end and having an external data connector;
   an optical window removably and sealingly mounted at the sheath distal end; and an optical module removably disposed within the sheath distal end and comprising an integrated image sensor, an optical lens, and a module connector configured for selective mechanical and electrical disconnection from and reconnection to a mating line connector in electrical communication with the external data connector.
2. The endoscope of example 1 being a flexible or rigid endoscope.
3. The endoscope of example 1 or 2 being a diagnostic or therapeutic endoscope.
4. The endoscope of any one of examples 1-3 wherein the image sensor and the optical lens are separated by a fixed distance.
5. The endoscope of any one of examples 1–4 wherein the optical module further comprises physical features for alignment and mating with corresponding physical features on the outer sheath.
6. The endoscope of any one of examples 1-5 wherein the optical module is sealed to prevent fluid or tissue ingress.
7. The endoscope of any one of examples 1-6 wherein the optical module is sealed to prevent condensation from forming therein during clinical use.
8. The endoscope of any one of examples 1-7 wherein the optical module further comprises an integral illumination source.
9. The endoscope of any one of examples 1-8 wherein a connection between the module connector and the line connector is waterproof or water resistant.
10. The endoscope of any one of examples 1-9 wherein a connection between the module connector and the line connector is a USB-type connection.
11. The endoscope of any one of examples 1-10 wherein the optical window is mounted at the sheath distal end using means configured for rapid exchange between clinical uses.
12. The endoscope of any one of examples 1-11 wherein the sheath lumen contains an elongate core, electrical cabling, and/or illumination sources.
13. The endoscope of any one of examples 1-12 wherein the sheath lumen is usable for receiving air, fluids, or operative tools therethrough.
14. The endoscope of any one of examples 1-13 wherein the sheath lumen further comprises a plurality of lumens.
15. The endoscope of any one of examples 1-14 further comprising an RFID tag or other identification device disposed therein and characterized for quantifying the number of endoscopes in a container without requiring physical, manual counting.
16. The endoscope of any one of examples 1-15 further comprising an RFID chip or other technology that prevents the endoscope from functioning after a single use.
17. The endoscope of any one of examples 1-16 further comprising a memory module adapted to collect and record performance information from the device during clinical use.
18. The endoscope of any one of examples 1-17 further comprising a memory module to record identifying information for components used in the endoscope.
19. The endoscope of any one of examples 1-18 wherein the outer sheath can be opened at the distal end, the proximal end or both ends to facilitate access, removal, and replacement of one or more internal subcomponents for testing, harvesting, or replacement thereof
20. The endoscope of any one of examples 1-19 further comprising unique visible or virtual markings on one or more components, the markings being configured for tracking repeated utilization of the one or more components.
21. A system configured for electric communication with the endoscope of any one of examples 1-20, the system having testing software to assess performance of the optical module.
22. A system for use with the endoscope of any one of examples 1-20, the system comprising: processing equipment configured to perform one or more steps that decontaminate, clean, disassemble, and reassemble the endoscope autonomously, semi-autonomously or under manual control.
23. An endoscope, comprising:
   an elongate body having proximal and distal ends and having one or more channels therethrough for a receiving an elongate core, cabling, and/or illumination sources;
   an outer protective sheath sealingly and removably surrounding the elongate body, the outer protective sheath having externally exposed markings and/or physical features for the endoscope to be tracked, aligned, and mated to manufacturing and reprocessing equipment;

an optical module disposed at the body distal end and being in electrical communication with at least one connector disposed at the body proximal end the optical module consisting of an integrated image sensor, an optical lens, and/or an illumination source;

wherein the optical module is attached to the outer sheath via a mount configured to permit selective mechanical disconnection and reconnection between the module and the sheath, the mount further being configured to permit selective electrical disconnection and reconnection between the module and the at least one connector disposed at the body proximal end; and a protective, non-optical lens at the body distal end configured to protect the proximally adjacent optical lens.

24. A method of handling an endoscope, the method comprising:
a first party manufacturing the endoscope according to proprietary manufacturing specifications of the first party;
the first party providing the endoscope to a second party in a sterile, ready-for-use condition;
the first party obtaining the endoscope from the second party after it has been used in a clinical setting;
the first party preparing the endoscope or parts thereof for subsequent clinical use by:
cleaning and decontaminating the endoscope;
testing system and component performance by connecting the endoscope to a proprietary and automated firmware and software testing protocol;
performing automated visual assessment of an outer body of the endoscope to assess for defects, markings, scratches or indentations from shipping or use that would visually deviate from original de novo parts;
removing an optical window from an endoscope sheath distal end;
removing and electrically disconnecting an optical module from the endoscope;
requalifying the optical window and the optical module against the proprietary manufacturing specifications of the first party;
electrically connecting and assembling a qualified optical module or a new optical module in the endoscope;
assembling an optical window on the endoscope sheath distal end; and
the first party packaging and sterilizing the prepared endoscope thereby restoring the medical device to the sterile, ready-for-use condition.

25. The method of example 24 wherein requalifying the optical window and the optical module comprises testing the optical window and the optical module to result in a decision regarding reuse or replacement of each of the optical window and the optical module.

26. The method of either example 24 or 25 wherein preparing the endoscope or parts thereof for subsequent clinical use further comprises cleaning and de-contaminating the endoscope or parts thereof.

27. An automated system for reprocessing an endoscope, the system comprising:
one or more sensors and/or physical features for tracking and/or aligning with respective external markings and physical features on the external surface of the endoscope;
a tool adapted for removing and replacing an optical window on an endoscope sheath distal end;
a tool adapted for removing and electrically disconnecting an optical module from the endoscope after removal of the optical window;
an optical tester adapted for qualifying the removed optical window against a specification therefor;
a module tester adapted for qualifying the removed optical module against a specification therefor; and
a tool adapted for electrically connecting and assembling an optical module in the endoscope.

28. A method of handling an endoscope, the method comprising:
a first party manufacturing the endoscope according to proprietary manufacturing specifications of the first party;
the first party providing the endoscope to a second party in a sterile, ready-for-use condition;
the first party obtaining the endoscope from the second party after it has been used in a clinical setting;
the first party preparing the endoscope or parts thereof for subsequent clinical use; and the first party packaging and sterilizing the prepared endoscope thereby restoring the medical device to the sterile, ready-for-use condition.

29. The method of example 28 wherein the endoscope being used in a clinical setting further comprises the endoscope being used only one time in a clinical setting before being obtained from the second party by the first party.

30. The method of either example 28 or 29 wherein, after it has been used in a clinical setting, the endoscope is in a non-sterile condition.

31. The method of any one of examples 28-30 wherein, after it has been used in a clinical setting, at least one surface of the endoscope is contaminated with bodily fluids.

32. The method of any one of examples 28-31 wherein preparing the endoscope further comprises decontaminating and cleaning the endoscope obtained from the second party.

33. The method of any one of examples 28-32 wherein preparing the endoscope further comprises disassembling the endoscope obtained from the second party.

34. The method of any one of examples 28-33 wherein disassembling the endoscope further comprises processing parts of the endoscope for recycling, waste, or re-use.

35. The method of any one of examples 28-34 wherein preparing the endoscope further comprises requalifying parts of the used endoscope for subsequent clinical use according to the proprietary manufacturing specifications.

36. The method of any one of examples 28-35 wherein preparing the endoscope further comprises requalifying the prepared endoscope according to the proprietary manufacturing specifications of the first party.

37. The method of any one of examples 28-36 wherein the endoscope is configured for using one or more automated or semi-automated process steps in preparing the endoscope for subsequent clinical use.

38. A method of providing an endoscope, the method comprising:
a first party manufacturing the endoscope according to proprietary manufacturing specifications of the first party;

the first party selling the endoscope at a selling price to a second party in a sterile, ready-for-use condition;
the first party obtaining the endoscope from the second party after it has been used in a clinical setting;
the first party providing a credit amount to the second party upon obtaining the endoscope therefrom;
the first party preparing the endoscope or components of the endoscope for subsequent clinical use;
the first party packaging and sterilizing the prepared endoscope thereby restoring the endoscope to the sterile, ready-for-use condition; and
the first party selling the restored endoscope to the second party.

39. The method of example 38 wherein the credit amount provided by the first party to the second party is less than the selling price of the endoscope exchanged when the endoscope was sold by the first party to the second party.

40. The method of either example 38 or 39 wherein the credit amount provided by the first party to the second party is in the form of a refund, a rebate, a credit-on-account, or discount voucher.

41. The method of any one of examples 38-40 wherein the credit amount is a variable amount dependent on the condition of the endoscope obtained by the first party from the second party.

42. A method of providing an endoscope, the method comprising:
a first party manufacturing an endoscope according to proprietary specifications of the first party;
the first party selling the endoscope at a selling price to a second party in a sterile, ready-for-use condition;
the first party obtaining the endoscope from the second party after it has been used in a clinical setting;
the second party subject to an additional fee should it not return the endoscope to the first party after it has been used in a clinical setting;
the first party preparing the endoscope or parts of the endoscope for subsequent clinical use;
the first party packaging and sterilizing the prepared endoscope thereby restoring the endoscope to the sterile, ready-for-use condition; and
the first party selling the restored endoscope.

43. The method of example 42 wherein selling the restored endoscope comprises the first party selling the restored endoscope to a third party.

44. The method of either example 42 or 43 wherein the selling price is a variable amount dependent on the condition of the endoscope obtained by the first party from the second party.

We claim:

1. A system comprising:
an external data connector; and
an endoscope including
an elongate outer sheath having a lumen extending between a proximal end and a distal end thereof,
an optical window removably and sealingly mounted at the distal end of the elongate outer sheath; and
an optical module removably disposed within the distal end of the elongate outer sheath, the optical module including
an integrated image sensor,
an optical lens, and
an optical module connector configured for selective mechanical and electrical disconnection from and reconnection to a mating line connector disposed within the distal end of the elongate outer sheath, wherein the mating line connector is in electrical communication with the external data connector via a cable and the cable includes sufficient slack length such that the mating line connector is configured to extend beyond the distal end of the elongate outer sheath during removal of the optical module through the distal end of the elongate outer sheath.

2. The system of claim 1, wherein the elongate outer sheath has external markings and/or physical features configured for tracking, aligning, and mating the elongate outer sheath to manufacturing and/or reprocessing equipment.

3. The system of claim 1, wherein the optical module further comprises physical features for alignment and mating with corresponding physical features on the elongate outer sheath.

4. The system of claim 1, wherein the optical module further comprises an integral illumination source.

5. The system of claim 1, wherein the lumen of the elongate outer sheath contains at least one of an elongate core, the cable, and an illumination source.

6. The system of claim 1, wherein the lumen of the elongate outer sheath is configured for receiving air, fluids, or operative tools therethrough.

7. The system of claim 1, further comprising an RFID tag disposed therein and characterized for quantifying a number of endoscopes in a container without requiring physical, manual counting.

8. The system of claim 1, further comprising an RFID chip configured to prevent the endoscope from functioning after a single use.

9. The system of claim 1, further comprising a memory module adapted to collect and record performance information from the endoscope during clinical use.

10. The system of claim 1, further comprising a memory module to record identifying information for components used in the endoscope.

11. The system of claim 1, wherein the optical window and the optical module contain interlocking features.

12. The system of claim 1, wherein the optical module is press-fit into a receptacle of the optical window.

13. The system of claim 1, wherein a handle is disposed at the proximal end of the elongate outer sheath.

14. A system comprising:
at least one connector; and
an elongate body having a proximal end and a distal end, the elongate body having one or more channels therethrough adapted for a receiving one or more of air, fluids, operative tools, an elongate core, cabling, and/or illumination sources;
an outer protective sheath sealingly and removably surrounding the elongate body;
an optical module disposed at the distal end of the elongate body, the optical module being in electrical communication with the at least one connector and the optical module comprising an integrated image sensor, an optical lens, and/or an illumination source, wherein the optical module is attached to the elongate body via a mount configured to permit selective mechanical disconnection and reconnection between the optical module and the elongate body, the mount further being configured to permit selective electrical disconnection and reconnection between the optical module and the at least one connector, wherein the mount is in electrical communication with the at least one connector via a cable and the cable includes sufficient slack length such that the mount is configured to extend beyond the distal end of the elongate body during removal of the optical module through the distal end of the elongate body.

15. The system of claim 14, wherein the selective electrical disconnection and reconnection between the optical module and the at least one connector is provided by a USB-type connection.

16. The system of claim 14, wherein the outer protective sheath can be opened at a distal end, a proximal end or both ends to facilitate access, removal, and replacement of one or more internal subcomponents for testing, harvesting, or replacement thereof.

17. The system of claim 14, wherein the outer protective sheath has externally exposed markings and/or physical features to be tracked, aligned, and/or mated to manufacturing and/or reprocessing equipment.

18. The system of claim 14, wherein a non-optical lens is sealingly and removably attached to the outer protective sheath distally adjacent the optical lens of the optical module.

19. The system of claim 14, wherein an optical window is removably and sealingly mounted at the distal end of the elongate body, and the optical window and the optical module contain interlocking features.

20. The system of claim 14, wherein the optical module is press-fit into a receptacle of an optical window removably and sealingly mounted at the distal end of the elongate body.

* * * * *